(12) United States Patent
Saha et al.

(10) Patent No.: US 8,345,231 B2
(45) Date of Patent: Jan. 1, 2013

(54) METHOD OF DETERMINING DEFECTS IN A SUBSTRATE AND APPARATUS FOR EXPOSING A SUBSTRATE IN A LITHOGRAPHIC PROCESS

(75) Inventors: Nilay Saha, Eindhoven (NL); Hermen Folken Pen, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 154 days.

(21) Appl. No.: 12/470,848

(22) Filed: May 22, 2009

(65) Prior Publication Data

US 2009/0296090 A1 Dec. 3, 2009

Related U.S. Application Data

(60) Provisional application No. 61/129,016, filed on May 30, 2008.

(51) Int. Cl.
*G01N 21/00* (2006.01)
(52) U.S. Cl. ............... 356/237.2; 356/237.4; 356/237.5
(58) Field of Classification Search ................ None
See application file for complete search history.

(56) References Cited

U.S. PATENT DOCUMENTS

| | | | | |
|---|---|---|---|---|
| 3,790,287 | A * | 2/1974 | Cuthbert et al. ............... 356/446 |
| 4,376,583 | A * | 3/1983 | Alford et al. ................ 356/237.2 |
| 4,659,220 | A * | 4/1987 | Bronte et al. ............... 356/237.5 |
| 5,822,055 | A * | 10/1998 | Tsai et al. ................... 356/237.1 |
| 5,914,495 | A * | 6/1999 | Ishizuka et al. .......... 250/559.45 |
| 5,923,554 | A * | 7/1999 | Nakata ........................ 700/110 |
| 5,982,921 | A * | 11/1999 | Alumot et al. ................ 382/145 |
| 6,249,347 | B1 * | 6/2001 | Svetkoff et al. ............... 356/625 |
| 6,414,483 | B1 | 7/2002 | Nath et al. |
| 6,509,966 | B2 * | 1/2003 | Ishiguro ..................... 356/237.2 |
| 6,521,889 | B1 | 2/2003 | Ina et al. |
| 6,617,603 | B2 * | 9/2003 | Ishiguro et al. .......... 250/559.45 |
| 6,924,884 | B2 * | 8/2005 | Boonman et al. ............... 355/55 |
| 7,012,672 | B2 * | 3/2006 | Van Rhee et al. ............... 355/53 |
| 7,019,815 | B2 * | 3/2006 | Jasper et al. .................... 355/55 |
| 7,113,257 | B2 * | 9/2006 | Brinkhof et al. ................ 355/53 |
| 7,173,270 | B1 | 2/2007 | Bruinsma et al. |
| 7,239,368 | B2 * | 7/2007 | Oesterholt et al. .............. 355/52 |
| 7,292,351 | B2 * | 11/2007 | Schoonewelle et al. ....... 356/601 |
| 7,599,054 | B2 * | 10/2009 | Takeda et al. .............. 356/237.5 |

(Continued)

FOREIGN PATENT DOCUMENTS

CN 1339701 A 3/2002

(Continued)

OTHER PUBLICATIONS

Office action in related Chinese application No. 200910142608.7 issued Mar. 9, 2011.

(Continued)

*Primary Examiner* — Gordon Stock, Jr.
(74) *Attorney, Agent, or Firm* — Pillsbury Winthrop Shaw Pittman LLP

(57) ABSTRACT

Method of determining defects in a substrate, the method comprising: scanning a scan range of the substrate with a sensor, the sensor projecting a beam of radiation on the substrate; measuring the fraction of the intensity of the radiation reflected from different substrate areas along the scan range; determining the variations of the measured fraction across the scan range; determining from the variations whether any defects are present in the substrate.

14 Claims, 6 Drawing Sheets

U.S. PATENT DOCUMENTS

| | | | |
|---|---|---|---|
| 7,659,988 B2 | 2/2010 | Kok et al. | |
| 7,756,318 B2 | 7/2010 | Nakatani | |
| 7,813,539 B2 * | 10/2010 | Shibuya et al. | 382/141 |
| 7,968,354 B1 * | 6/2011 | Haller et al. | 438/14 |
| 8,018,585 B2 * | 9/2011 | Hariyama et al. | 356/237.2 |
| 2002/0106848 A1 | 8/2002 | Wack et al. | |
| 2004/0189964 A1 | 9/2004 | Nijmeijer et al. | |
| 2005/0024632 A1 | 2/2005 | Plemmons et al. | |
| 2006/0085155 A1 * | 4/2006 | Miguelanez et al. | 702/118 |
| 2006/0152716 A1 * | 7/2006 | Meeks | 356/237.2 |
| 2007/0146695 A1 * | 6/2007 | Brouwer et al. | 356/237.4 |
| 2007/0153273 A1 | 7/2007 | Meeks | |
| 2007/0179740 A1 | 8/2007 | Bell et al. | |
| 2008/0002207 A1 | 1/2008 | Kok et al. | |
| 2008/0079920 A1 * | 4/2008 | Hommen et al. | 355/55 |

FOREIGN PATENT DOCUMENTS

| | | |
|---|---|---|
| CN | 1542551 | 11/2004 |
| EP | 1457828 A | 9/2004 |
| JP | 2-233176 | 9/1990 |
| JP | 2-237678 | 9/1990 |
| JP | 6-020913 | 1/1994 |
| JP | 6-223418 | 8/1994 |
| JP | 9-106075 | 4/1997 |
| JP | 10-043666 | 2/1998 |
| JP | 2002-008972 A | 1/2002 |
| JP | 2002-064049 | 2/2002 |
| JP | 2002-190446 | 7/2002 |
| JP | 2003-234278 | 8/2003 |
| JP | 2001-116529 A | 4/2004 |
| JP | 2007-088465 A | 4/2004 |
| JP | 2005-128516 | 5/2005 |
| JP | 2007-057521 | 3/2007 |
| JP | 2007-286000 A | 11/2007 |
| JP | 2008-003111 A | 1/2008 |
| JP | 2008-004928 | 1/2008 |
| JP | 2008-016840 | 1/2008 |
| WO | 2007/075082 A1 | 7/2007 |

OTHER PUBLICATIONS

Office action in related Korean application No. 10-2009-0047698 dated Feb. 18, 2011.

Extended European Search Report issued on Jul. 14, 2009 in European Application No. 09160128.6-1226.

Office Action in related Chinese application No. 200910142608.7 issued Sep. 27, 2010.

Office Action in related Japanese Application No. 2009-123725 mailed Aug. 29, 2011.

Japanese Office Action dated Jul. 12, 2012 in corresponding Japanese Patent Application No. 2009-123725.

* cited by examiner

METHOD OF DETERMINING DEFECTS IN A SUBSTRATE AND APPARATUS FOR EXPOSING A SUBSTRATE IN A LITHOGRAPHIC PROCESS

RELATED APPLICATION

The present invention claims benefit under 35 U.S.C. §119 (e) from U.S. Provisional Application No. 61/129,016 filed on May 30, 2008, which is incorporated herein by reference in its entirety.

FIELD

The present invention relates to a method of determining defects in a substrate. The invention also relates to an apparatus for exposing a substrate in a lithographic process.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

The lithographic apparatus may be of a type wherein an optical projection system is used to project a pattern imparted on a radiation beam by a patterning device, for instance a mask, onto a target portion of a substrate, as will be explained later. An optical projection lithographic apparatus may furthermore be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Furthermore, the lithographic apparatus may be of a type having two (dual stage) or more substrate tables supporting a plurality of substrates (and/or two or more mask tables). In such "multiple stage" machines the additional tables may be used in parallel, or preparatory steps may be carried out on one or more tables (i.e., in a preparatory stage or measurement stage), while one or more other tables are being used for exposure of one or more substrates (i.e., in an exposure stage).

An example of a preparatory step carried out in the measurement stage of an optical projection lithographic apparatus is the measurement of the distance between the optical projection system and the substrate to be exposed. The best resolution of an projection image is made when the substrate is in focus of the optical projection system. In order to obtain a good focus, the substrate should be positioned at the focal point of the optical system. In order to maintain the substrate surface within the focus of the projection system, the distance of the substrate from the optical system (especially the projection lens) should be determined accurately. To this end a lithographic apparatus may comprise a sensor for measuring the height of the surface of the substrate.

Currently a sensor for measuring the height of the substrate is used as a tool to measure the local height and tilt at a large number of measurement points on the surface of the substrate. In a typical dual stage lithographic apparatus, for instance the ASML Twinscan, the height information that is gathered in the measurement stage by the sensor (eg. the level sensor), is forwarded to the exposure stage and used during exposure of the substrate. In other types of lithographic apparatus the sensor, sometimes called the "focus sensor", is configured to perform the substrate height measurements on the fly, that is during exposure of the substrate.

Although the height of the surface of the substrate is measured, the sensor fails to detect defect patterns present on the substrate. Defects typically occur at the substrate edges due to processing problems. Earlier in dry machines this was less of a problem as during exposure the substrate normally did not come into physical contact with the lithographic apparatus. In immersion type lithographic apparatus, because of the contact of the substrate with immersion water, there is a risk that defects might spread to other portions of the substrate, which may lead to further damage to the substrate and contamination of the lithographic apparatus as the process layers are peeled off from the substrate and flow with immersion liquid to various parts of the apparatus.

SUMMARY

It is desirable to provide an improved method and apparatus for detecting defects in a substrate.

According to an embodiment of the invention there is provided a method of determining defects in a substrate, the method comprising:
- scanning a scan range of the substrate with a sensor, the sensor projecting a beam of radiation on the substrate;
- measuring the fraction of the intensity of the radiation reflected from different substrate areas along the scan range;
- determining the variations of the measured fraction across the scan range;
- determining from the variations whether any defects are present in the substrate.

According to a further embodiment of the invention there is provided an apparatus for exposing a substrate in a lithographic process, comprising:
- a substrate table constructed to hold a substrate;
- a sensor arranged and construed to project a measurement beam of radiation on the substrate,
- a controller for controlling the relative positions of the substrate table and the sensor, the controller being configured so as to have the sensor scan a scan range of the substrate with said measurement beam of radiation;
- wherein the sensor is arranged and constructed to measure the fraction of the intensities of radiation reflected from different substrate areas along the scan range and wherein the controller is configured so as to determine the variations of the fraction across the scan range and to determine from the fraction whether any defects are present in the substrate.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
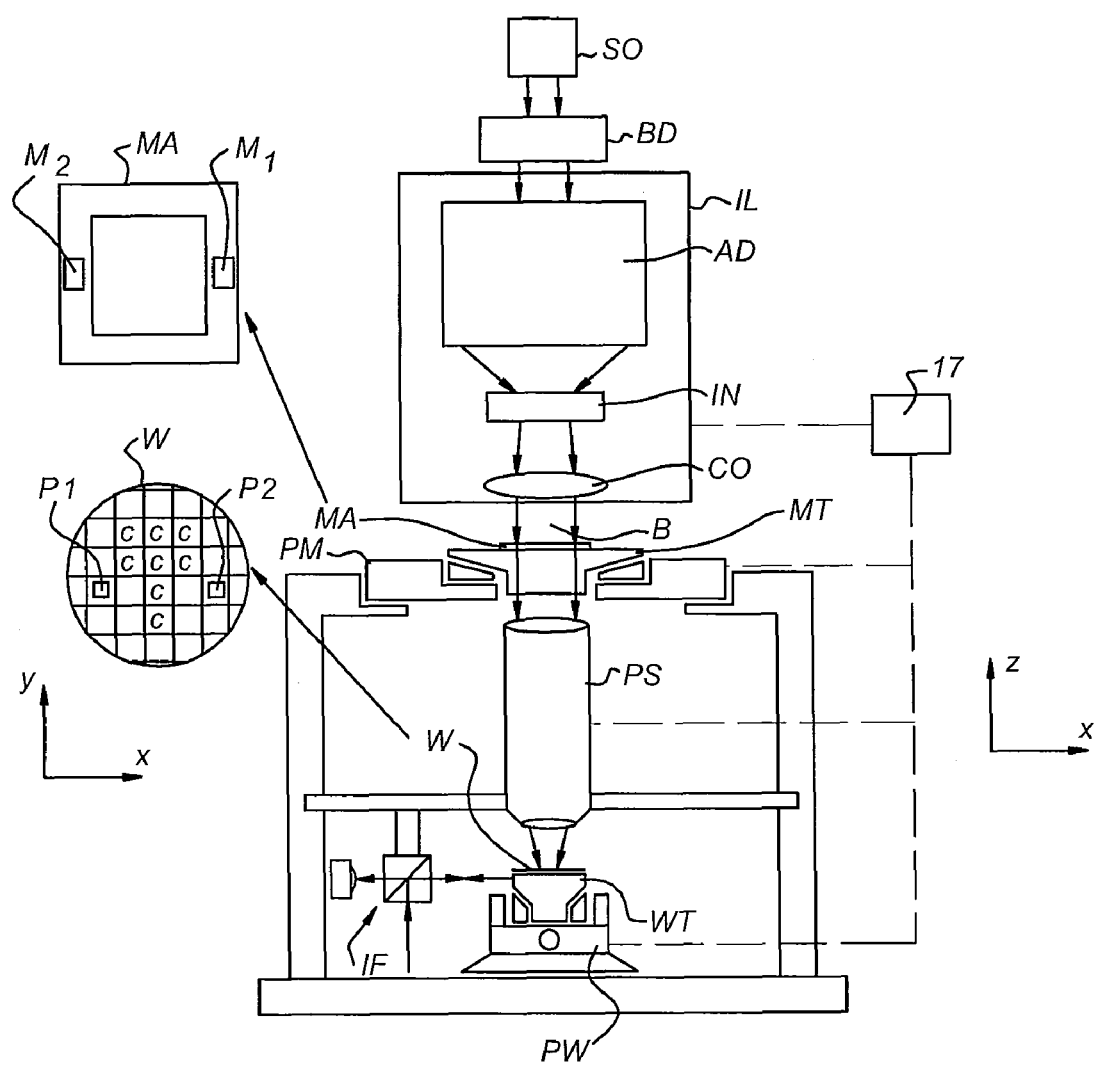
FIG. 1 depicts a lithographic apparatus according to an embodiment of the invention.

FIG. 1 schematically depicts a lithographic apparatus according to one embodiment of the invention. The apparatus comprises:
- an illumination system (illuminator) IL configured to condition a radiation beam B (e.g., UV radiation).
- a support structure (e.g., a mask table) MT constructed to support a patterning device (e.g., a mask) MA and connected to a first positioner PM configured to accurately position the patterning device in accordance with certain parameters;
- a substrate table (e.g., a wafer table) WT constructed to hold a substrate (e.g., a resist-coated wafer) W and connected to a second positioner PW configured to accurately position the substrate in accordance with certain parameters; and
- a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2A:
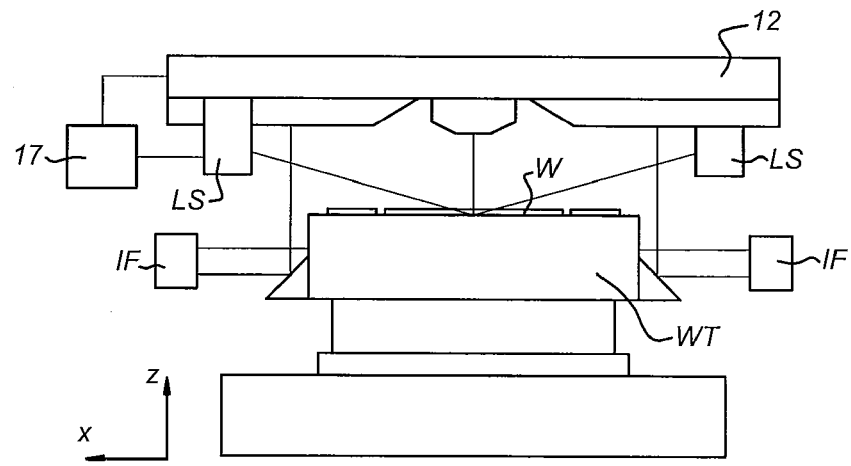
FIGS. 2a and 2b show a schematic representation of a part of a dual stage lithographic apparatus, including a sensor.
Figure 2B:
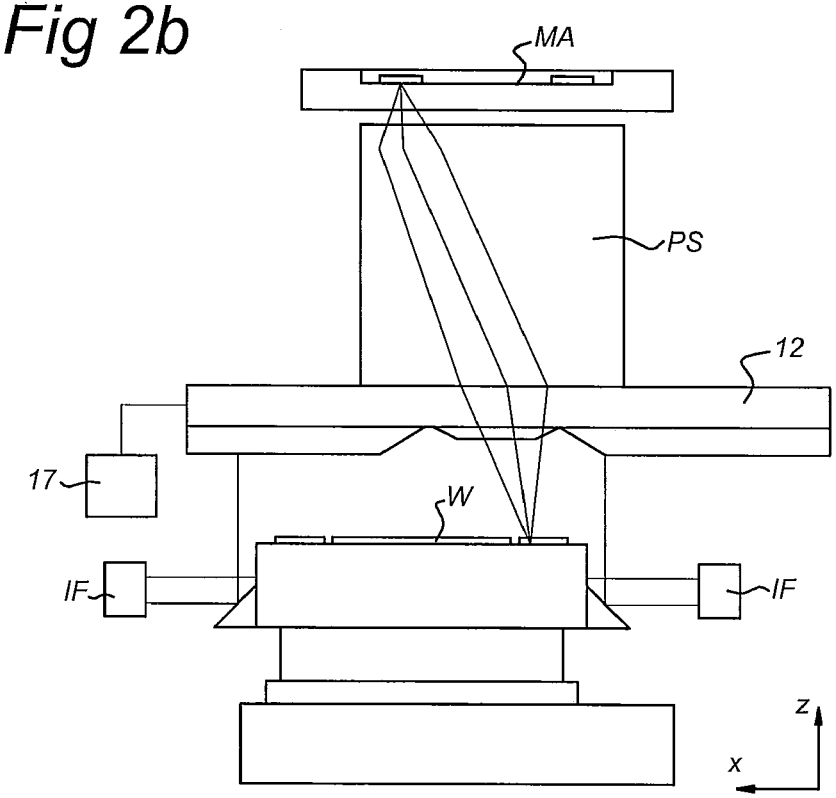

A height sensor measures the heights of substrates or of areas on the substrate table. Both FIGS. 2A and 2B show a schematic representation of a part of an embodiment of a dual stage lithographic apparatus, including a height sensor or level sensor LS. FIG. 2A shows the first stage or measurement stage of the apparatus, while FIG. 2B shows the second or exposure stage of the apparatus. In the embodiment the first and second stages of the apparatus are arranged side by side. Several components in the measurement stage are similar or even identical to the components present in the exposure stage of the apparatus and most of them have already been described in connection with the (one-stage) lithographic apparatus of FIG. 1. A detailed description thereof is therefore omitted here.

Figure 3:
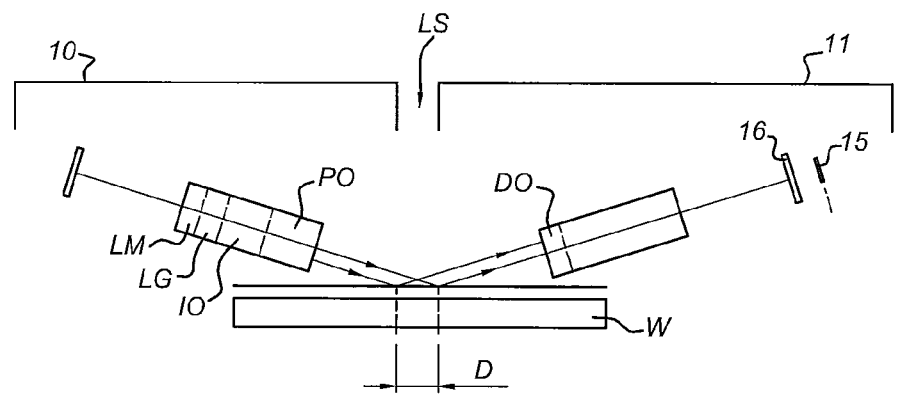
FIG. 3 is a schematic representation of the measurement setup of a sensor.

In the embodiment shown a height sensor is only present in the measurement stage. The configuration makes it possible to make a substrate map, including a height map, of a substrate, while a previous substrate is being exposed. Referring to FIG. 3, the sensor is level sensor LS and comprises a projection branch 10 and a detection branch 11, both being mounted on metrology frame 12. The projection branch 10 comprises an illumination assembly and projection optics (PO). The illumination assembly includes a module for generating a measurement beam of radiation, in the present embodiment a lamp module (LM) for generating a light beam, a light guide (LG) and illumination optics (IO). The lamp module comprises one or more halogen lamps mounted on a position-switching mechanism. The light guide comprises optical fibers that are used to transport the light from the halogen lamp to the illumination optics (IO) of the sensor. One of the illumination optics is designed to focus the light from the light guide on the projection grating. It comprises a number of lenses to focus the lights and an end mirror to bend the light towards the projection grating.

The projection optics (PO) module comprises a projection grating and a sensor lens assembly. The sensor lens assembly comprises mirrors to project an image of the projection grating to the substrate. The projected image includes the grating used by a capture system for coarse measurements of the height and the grating used by the a measure system for fine measurements of the height.

The detection branch 11 comprises a detection optics (DO) module, including a lens assembly, a detection grating 16 and several further optical elements such as modulation optics. The detection branch 11 also comprises a data acquisition module (LSDAM), including a detector 15. The lens assembly of the detection optics is similar to the lens assembly of the projection optics (PO). The detection grating 16 splits the reflected light beam into three spots to be detected by the detector assembly 15 of the capture system and nine spots to be detected by the detector assembly 15 of the measure system. The capture system is intended to provide for a coarse measurement of the height (and the tilt) of the substrate. The function of the capture system is to bring the substrate into the measurement range of the measure system, i.e., the measurement result of the capture system is used to move the substrate to a height level that is within the tolerance of the measure system. The measure system then provides for a more accurate height measurement of the exposure fields of the substrate. The data representative of the more accurately measured heights (i.e., the substrate height map) is transfered to a control system or controller 17 (schematically shown in FIGS. 1 and 2) of the lithographic apparatus. Once the substrate is in the exposure stage the recorded substrate height map is used to control the substrate table and level the substrate during exposure.

In operation, the surface of which the height is to be measured, is brought in a reference position and is illuminated with the measurement light beam. The measurement light beam impinges on the surface to be measured at an angle which is less than 90 degrees. Because the angle of incidence is equal to the angle of reflection, the measurement light beam is reflected back from the surface with the same angle to form a reflected beam of radiation, as is shown in FIG. 3. The measurement light beam and the reflected light beam define a measurement plane. The sensor measures the position of the reflected measurement light beam in the measurement plane. If the surface is moved in the direction of the measurement light beam and another measurement is done, the reflected beam of radiation is reflected in the same direction as before. However, the position of the reflected beam of radiation has shifted the same way the surface has been moved.

The sensor may be moveable with respect to the substrate table. In other embodiments, however, the substrate table (WT) is moveable with respect to the sensor. The substrate table can move in at least the lateral direction (i.e., a direction X and a direction Y) with respect to the sensor. The measurement of the position of the reflected measurement light beam in the measurement plane is repeated for a number of different lateral positions. More specifically, a plurality of height positions is measured by the sensor (possibly in combination with one or more Z-interferometers and the lateral positions associated with each of the height positions are measured by the position sensor IF (for instance comprising one or more interferometers).

In an embodiment, the level sensor (optionally in combination with Z-interferometers) in addition to detecting the height of the substrate surface, may be used to detect the fraction of the intensity of the measurement light beam as reflected (or, more generally, the reflected beam of radiation). Referring to FIG. 3, the detected intensity signal is basically a signal that is a convolution of the LS spot intensity signal and the reflectivity of the structure on the substrate. In this embodiment the radiation incident on the substrate is considered to be constant. Thus in the embodiment the reflected intensity implicitly represents the fraction although there is a constant ratio between them. The intensity signal obtained by moving a sensor spot across the substrate (or moving the substrate with respect to the levels sensor or moving both the sensor and the substrate) is proportional to the effective spot width.

$$I(x) = \int_{t=0}^{t=D} r(x, t) I(t) dt$$

$r(x, t)$ = reflectivity $I(t)$ = Light intensity.

Referring the FIG. 3 and to the above equation the intensity at any point x on the substrate's surface is an integral of the reflectivity r(x,t) of surface and the intensity I(t) of the beam over the spot width D of the sensor. If the structure on the substrate is large enough (for instance larger than approximately 0.1 mm, depending on the accuracy of the sensor), this structure can be seen in the intensity signal.

Figure 4:
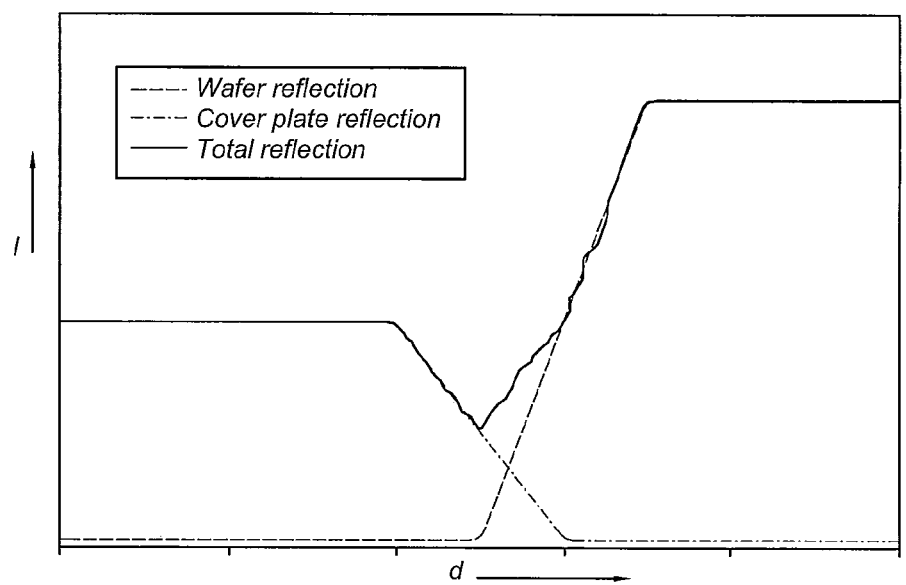
FIG. 4 is a graphical representation of the intensity signal of the sensor as function of the distance from the center of the substrate, when scanned across the substrate edge.
Figure 5:
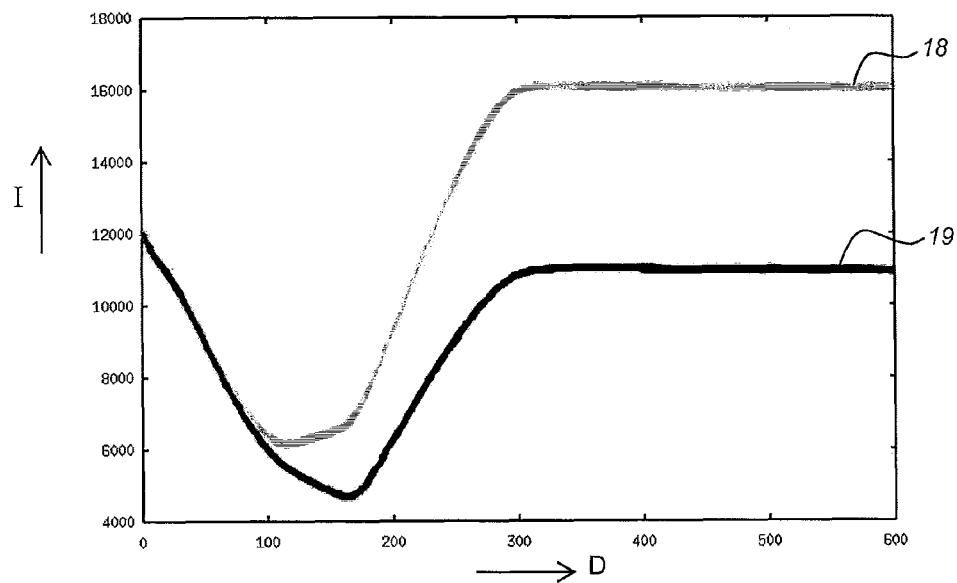
FIG. 5 is a graphical representation of the intensity signal of the sensor, for a non-processed substrate and for a processes substrate.

FIG. 4 shows a graph of the intensity signal (I) measured by the sensor as a function of the distance d from the centre of a substrate when an ultra flat substrate with no process layer is scanned in a radial direction, between the centre of the substrate and a position past the substrate edge. As shown in FIG. 4, when the substrate is scanned from the BES ring towards the center of the substrate, the resultant profile (denoted by "total reflection") results from the change in reflectivity as one goes from the substrate (right) to the mirror block (left). When the radiation spot reaches the edge of the substrate a part of the radiation spot impinges partly on the substrate and partly outside the substrate. Then in this embodiment the part of the spot on the substrate has the largest contribution to the reflected intensity. However, when the substrate is processed and has a top coating of resist on it, then the substrate surface reflectivity goes down dramatically and the reflectivity on the mirror block is higher than that on the substrate, as is depicted in FIG. 5. Herein curve 18 represents an ultra flat, non-processed substrate, while curve 19 represents a processed substrate that does not have any defects. Clearly is visible that the reflectivity of the processed substrate curve 19 decreases as a result of the processing of the substrate surface.

Figure 6:
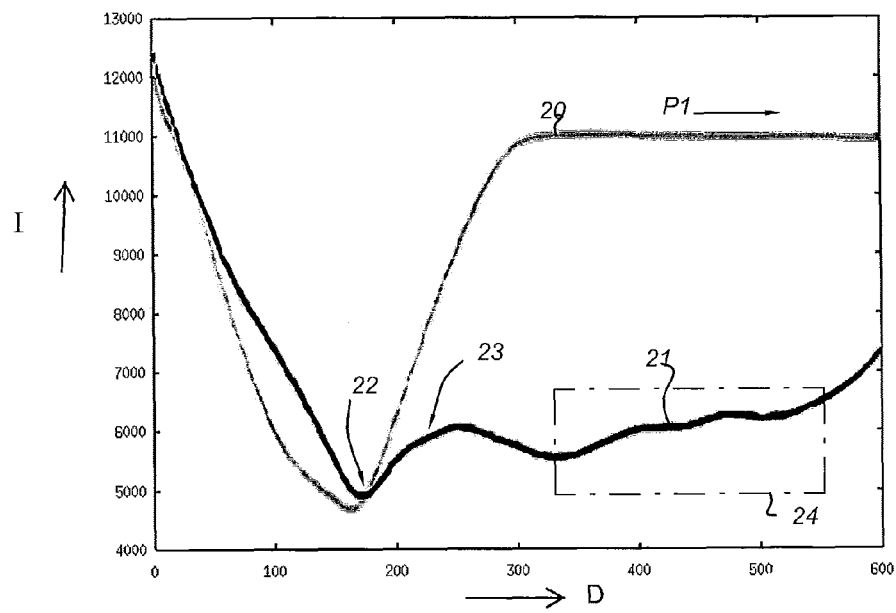
FIG. 6 is a graphical representation of the intensity signal of the sensor, for a processed non-defective substrate and for a processed defective substrate.

Consequently, when the substrate has been exposed and processed, the reflectivity of the substrate may be reduced considerably. Plots of the intensity versus the distance from a position outside a substrate towards the centre thereof (direction $P_1$ is towards the centre of the substrate) for another processed "good" substrate (practically without defects) and a "bad' substrate (with defects) are shown in FIG. 6. Plot 20 shows the intensity of the processed "good" substrate, while plot 21 represents the "bad" substrate. From left to right the plots show the presence of the BES ring (the BES ring being a metal ring at the periphery of the substrate table), of a gap between the BES ring and the substrate and of the substrate itself. The dip 22 in the plot is when the sensor spot falls on the gap between the wafer and the BES ring. Closer to the centre of the substrate the curve 20 of the "good' substrate shows a substantially flat region. However, the curve 21 for the "bad" substrate has a region 24 wherein the intensity shows a varying, wiggly behavior. This region 24 is representative of structures, for instance holes or other types of damage, on the surface of the substrate.

Figure 7:
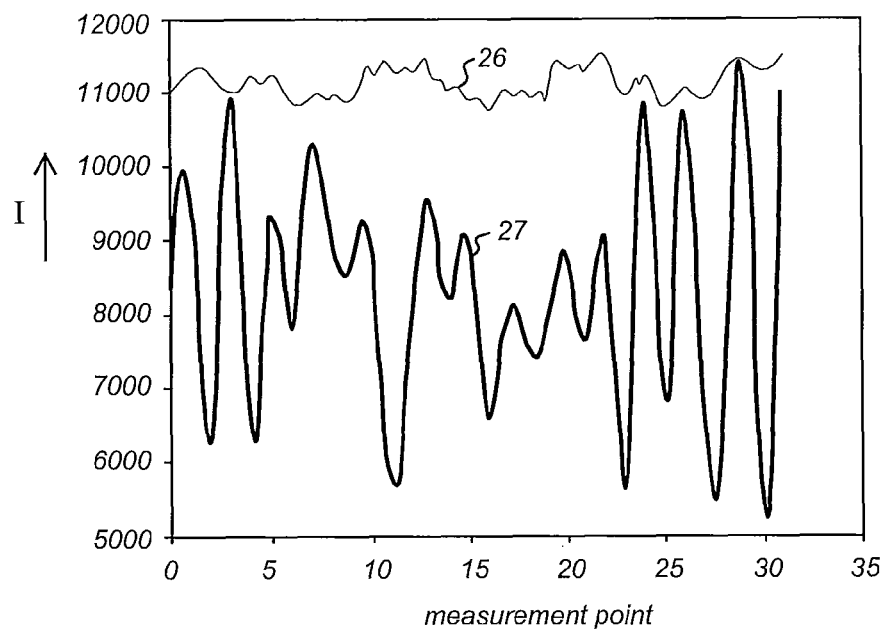
FIG. 7 is a graphical representation of the intensity signal of the sensor, taken at short distance from the circumferential edge of the substrate.

FIG. 7 shows plots of the intensity versus distance along a circle with a radius almost equal to or slightly less (e.g., 1.2 mm) than the radius of the substrate (i.e., 300 mm). The results of intensity measurements of the above-discussed radial edge scans performed at different angular positions of the substrate have been rearranged so that the intensities at different angular positions along a circular trajectory close the circumferential edge of the substrate could be collected. The circular ring intensities have been reconstructed by taking intensity data at a fixed distance (for instance about 1.3 mm) from the edge of wafer. The results of the reconstruction are shown in FIG. 7. Curve 26 represents the intensities in a circle around the centre of the substrate close to the edge thereof in case of a processed "good" substrate. Curve 27 represents the intensities along the same trajectory, but associated with a "bad" substrate or a defective substrate, i.e., a substrate on which defects are present. It is clear from FIG. 7 that for a defective substrate the edge intensity has a wide variation, in comparison to the edge intensity of a good substrate. The standard deviation of the defective substrate is, in the present example, about 1864. The standard deviation of the good substrate is about 216. In the present example the ratio |std_dev_bad_wafer-std_dev_good_wafer|/(std_dev_good_wafer) is about 7. This ratio has proven to provide a good indication of the quality of the substrate. By setting a threshold on the standard deviation itself or on this ratio a good substrate may be distinguished from a defective one. For the present example this could mean that by setting a threshold of, say, 2, the ratio would give a clear and direct indication that the substrate has defects.

Figure 8:
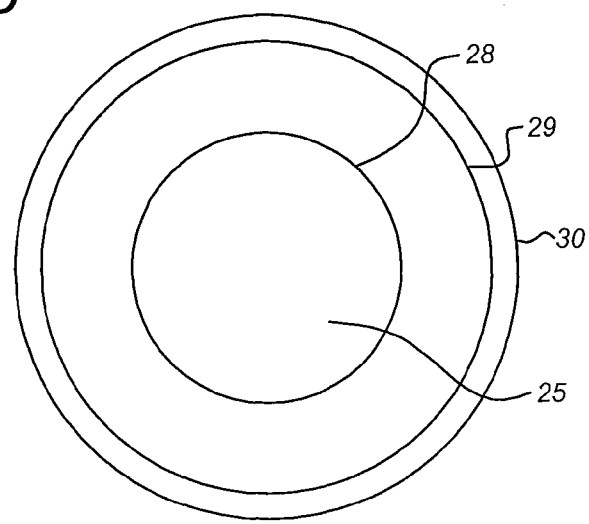
FIG. 8 is a top view of an embodiment of a substrate that is scanned along two concentric global level circle areas.
Figure 9:
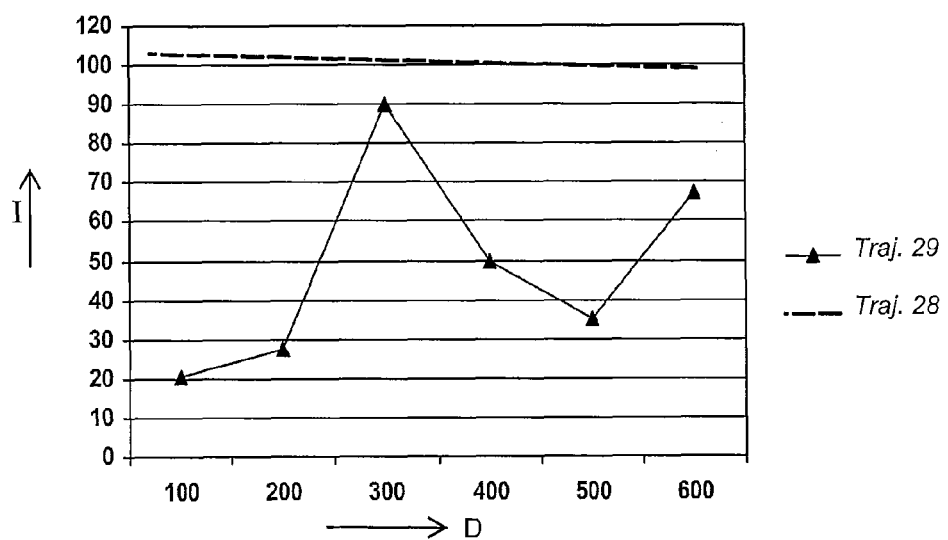
FIG. 9 is a graphical representation of the intensity signal of the sensor resulting from the scan process of FIG. 8.

In FIG. 8 a schematic top view of a substrate 25 is depicted. In this embodiment, using the sensor (LS), more specifically the capture system thereof, a global level circle (GLC) scan, also called a circular ring intensity measurement, may be performed at constant height above the surface of the substrate. The scan comprises two scan steps. In the first step the sensor (LS) measures the intensity of the reflected beam of radiation along an essentially circular trajectory 28 close to the centre of the substrate. Since the chance of defects being present in this part of the substrate, i.e., relatively close the centre of the substrate, is less, the intensity scan along trajectory 28 may be considered a reference scan. The resulting intensity signal of the sensor is depicted in FIG. 9. In a second step the sensor (LS) measures the intensity along a second trajectory 29 close to the circumferential edge 30 of the substrate 25. The resulting intensity signal of the sensor (LS) is depicted in FIG. 9 as well. From FIG. 9 already follows that scanning in the scan region near the circumferential edge of the substrate (which has circular edge effects) results in an intensity signal that shows far more variations than the intensity signal obtained when a scan close to the center of the substrate is performed, which provides a good indication whether or not the edge of the substrate is defective.

If defects occur in the substrate, these defect will probably occur close to the edge of the substrate and therefore the intensity scan close to the edge 30 of the substrate 25 may provide a good indication of the presence of any defects on the substrate. It will be apparent to the skilled person that the first and second step may be carried out in reverse order (i.e., the first step after the second step) and that other trajectories may be followed by the sensor (LS) to cover other reference regions and/or potentially defective regions.

Once both steps have been performed, a measure for the variation of the measured intensities may be determined. In an embodiment a measure for characterizing the variability may be the root mean square deviation (RMSD) of the signal across the scan range. In another embodiment a measure for the variation of the intensities is the standard deviation along a circular scan range. The standard deviation of intensities (GLC1) along the first circle 28 and the intensities (GLC2) along the second circle 29 can be calculated. The calculated standard deviation is then normalized using the intensities (GLC1) along the first trajectory 28, i.e., (GLC2−GLC1)/GLC1. Based on the normalized standard deviation an evaluation can be made whether or not the examined substrate has any defects.

One measure for evaluating the quality of the substrate is by comparing the standard deviation or the normalized standard deviation with a pre-set threshold. If the (normalized) standard deviation is larger than the threshold, the substrate may be considered to contain one or more defects. The substrate may then be rejected and further processing steps of the substrate, for instance an exposure step or a transfer to the next stage in case of a multiple stage lithographic apparatus, do not need to be carried out. If on the other hand the (normalized) standard deviation remains smaller than the threshold, the substrate is considered to be free of any substantial defects. The substrate may then be subjected to the next processing step.

Consequently, the method of determining defects in a substrate may comprise:
  providing a sensor construed for projecting a light beam on the substrate, detecting the reflected light intensity;
  scanning the substrate with said light beam in a predefined scan range;
  performing measurements of the intensities of light reflected from different substrate areas along the scan range;
  determine a measure for the variations of the light intensity across at least a part of the scan range;
  determining from the measure for the variations of the light intensity whether any defects are present.

The intensity information basically may give the integrated reflectivity of the scanned substrate and may be a measure of the total amount of reflected light received by the sensor detector. The amount of reflected light may be successfully used to detect defects on the surface of the substrate. Using this information from the reflected light received by the sensor detector a defect map of the substrate may be produced and based on the defect map a decision can be made whether to use the substrate, for instance in a subsequent exposure stage in case of a dual stage lithographic apparatus, or reject the wafer as being defective.

Determining a measure for the variations of the measured intensities may comprise:
  determining a measure for the average radiation intensity across at least a part of the scan range;
  determining a measure for the deviations of the measured intensities from the average radiation intensity measure;
  determining from the average radiation intensity measure and the radiation intensity deviation measure whether any defects are present.

In a further embodiment the average radiation intensity measure and the radiation intensity deviation measure may be determined on basis of the intensities measured in the same part of the scan range. That is that the intensities measured in the defective part of the substrate may be determined relative to the average intensity measured in the same defective part of the substrate.

The measure for the average radiation intensity and the measure for the deviation may be determined on basis of the intensities measured in the same part of the scan. Referring to FIG. 7, it is possible to perform measurements on the potentially defective area only, without also performing measurements in the reference area and to determine the quality of the substrate on basis of these measurements alone. For instance, the standard deviation for bad wafers may be 1864 and for good wafers 216. One can set the threshold, for instance at 800, and consider a wafer as a bad wafer if the deviation is larger than this threshold. In another embodiment the average radiation intensity measure is determined on basis of the intensities measured in a first part of the scan range, for instance the region defined by the inner circle 28 shown in FIG. 8, while the radiation intensity deviation measure is determined on basis of the intensities measured in a second, different part of the scan range, for instance the potentially defective region around the outer circle 29 of FIG. 8.

The determined deviation measure may further be normalized, for instance by dividing it by the standard deviation of intensities measured in the reference scan range. In another embodiment the deviation measure is divided by the measure for the average radiation intensity.

The measure for the variations of the measured radiation intensities may then be compared with a predefined threshold value. If the deviation measure exceeds the threshold value, the substrate my contain one or more defects, while in the opposite case one may consider the substrate to be substantially free from (substantial) defects.

The reference area and the possibly defective area may be present on the same substrate. In other embodiments, however, the reference area and defective area are present on different substrates. For instance in embodiments wherein a plurality of similar or identical substrates are manufactured, for all of the substrates use can be made of the intensities measured in a reference area of only one of the substrates.

Although the intensity of the light beam reflected from the substrate may be used by a height sensor already present in the apparatus, for instance a level sensor for measuring the height of the substrate during a measurement phase or a focus sensor for measuring the height of the substrate during an exposure phase, in other embodiments a different type of sensor may additionally or alternatively be used. For instance, an intensity detector (sensor) especially configured for the purpose of measuring the intensity of a light beam reflected from the substrate may be used.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method of determining defects on a surface of a substrate, the method comprising:
    scanning a scan range of the substrate with a height sensor, the height sensor projecting a beam of radiation on the substrate at an angle of incidence less than 90 degrees;
    measuring, at an angle of reflection equal to the angle of incidence, a fraction of an intensity of the radiation reflected from different substrate areas along the scan range;
    determining variations of the measured fraction across the scan range;
    determining from the variations whether any defects are present on the surface of the substrate.

2. A method according to claim 1, wherein scanning the substrate comprises projecting the beam of radiation along the scan range by providing a relative movement between the sensor and the substrate.

3. A method according to claim 1, wherein measuring the fraction of intensity is performed in a measurement station of a lithographic exposure apparatus arranged to perform a substrate exposure.

4. A method as claimed in claim 1, comprising comparing the variations with a threshold variation value.

5. A method as claimed in claim 1, wherein a reference part of the scan range comprises at least one reference area of the substrate selected to be an area likely to be free of defects and a test part of the scan range comprises at least one potentially defective area of the substrate.

6. A method according to claim 1, wherein determining the variations comprises:
    determining an average fraction across at least a part of the scan range;
    determining deviations of the fraction from the average fraction; and
    using the deviations to determine whether any defects are present.

7. A method as claimed in claim 4, wherein determining the variations comprises calculating a variance of the radiation intensities measured along at least a part of the scan range.

8. A method according to claim 6, wherein the average fraction is determined on basis of intensities measured in a first part of the scan range, while the deviations are determined on basis of intensities measured in a second, different part of the scan range.

9. A method as claimed in claim 5, wherein the areas comprise concentric rings, the reference area being defined as an inner ring of the substrate and the potentially defective area being defined as an outer ring of the substrate not contiguous with the inner ring.

10. A method according to claim 6, wherein determining the deviations of the fraction comprises determining a difference between fractions measured in a further part of the scan range and the fraction measured in the at least a part of the scan range.

11. A method according to claim 6, wherein determining the presence of defects further comprises comparing the deviations with a threshold value for the deviations and determining whether the deviations exceed the threshold value.

12. An apparatus for exposing a substrate in a lithographic process, comprising:
    a substrate table constructed to hold a substrate;
    a height sensor arranged and constructed to project a measurement beam of radiation on the substrate at an angle of incidence less than 90 degrees,
    a controller for controlling relative positions of the substrate table and the sensor, the controller being configured so as to have the sensor scan a scan range of the substrate with said measurement beam of radiation;
    wherein the sensor is arranged and constructed to measure a fraction of the intensities of radiation reflected from different substrate areas along the scan range, at an angle of reflection equal to the angle of incidence, and wherein the controller is configured so as to determine variations of the fraction across the scan range and to determine from the variations whether any defects are present on the surface of the substrate.

13. Apparatus as claimed in claim 12, wherein the sensor is arranged and constructed to determine from the reflected radiation the height of the surface of the substrate arranged on the substrate table, and wherein the controller is configured so as to compare the variations of the fraction with a threshold variation value.

14. A method of detecting defects on a surface of a substrate, comprising:
    using a height sensor to project a beam of radiation on the substrate over a scan range of the substrate at an angle of incidence less than 90 degrees;
    measuring a fraction of an intensity of the radiation reflected from different substrate areas along the scan range, at an angle of reflection equal to the angle of incidence;
    measuring a fraction of an intensity of the radiation reflected from a reference area outside the scan range;
    determining variations of the measured fraction across the scan range and the measured fraction from the reference area; and
    determining from the variations whether any defects are present on the surface of the substrate, the determining including comparing the variations from the scan range with the variations from the reference area.

* * * * *